United States Patent [19]

Bertoli et al.

[11] Patent Number: 5,679,809
[45] Date of Patent: Oct. 21, 1997

[54] CONCENTRATE OF POLYUNSATURATED FATTY ACID ETHYL ESTERS AND PREPARATION THEREOF

[75] Inventors: Constantin Bertoli, Romanel S/Lausanne; René Fumeaux, Blonay, both of Switzerland; Marie-Claude Perrenoud Ferreira, Vila Nova de Foz Coa, Portugal; Junkuan Wang, Lausanne, Switzerland

[73] Assignee: Nestec S.A., Vevey, Switzerland

[21] Appl. No.: 418,588

[22] Filed: Apr. 6, 1995

[30] Foreign Application Priority Data

May 9, 1994 [EP] European Pat. Off. .............. 94107202

[51] Int. Cl.$^6$ .......................................... C11B 3/00
[52] U.S. Cl. .......................... 554/186; 554/167; 554/170; 554/175; 554/184
[58] Field of Search ................. 584/66, 68, 167, 584/170, 175, 184, 186

[56] References Cited

U.S. PATENT DOCUMENTS

| | | |
|---|---|---|
| 4,377,526 | 3/1983 | Fujita et al. .............................. 260/424 |
| 4,776,984 | 10/1988 | Traitler et al. . |
| 5,106,542 | 4/1992 | Traitler et al. .......................... 554/186 |
| 5,130,449 | 7/1992 | Lagarde et al. . |

FOREIGN PATENT DOCUMENTS 1240513  9/1968  United Kingdom .

*Primary Examiner*—Gary Geist
*Assistant Examiner*—Deborah D. Carr
*Attorney, Agent, or Firm*—Vogt & O'Donnell, LLP

[57] ABSTRACT

A composition concentrated in ethyl esters of polyunsaturated fatty acids is prepared by mixing a refined oil rich in polyunsaturated fatty acids with ethanol in the presence of a catalyst to obtain an ethanolyzate containing a glycerol phase and fatty acid ethyl ester phase. The fatty acid ethyl ester phase is separated from the glycerol phase and mixed with urea and ethanol to form a mixture, which is cooled to form a liquid phase containing fatty acid ethyl esters and a solid phase containing insoluble inclusion complexes. The liquid phase is separated from the solid phase to obtain a fraction enriched in ethyl esters of polyunsaturated fatty acids.

10 Claims, No Drawings

CONCENTRATE OF POLYUNSATURATED FATTY ACID ETHYL ESTERS AND PREPARATION THEREOF

BACKGROUND OF THE INVENTION

This invention relates to a process for the production of a concentrate of polyunsaturated fatty acids in the form of ethyl esters, more particularly essential fatty acids belonging to the small n-3 and n-6 families, more especially gamma-linolenic acid (GLA) linoleic acid (LA), eicosapentaenoic acid (EPA) and docosahexaenoic acid (DHA).

According to U.S. Pat No. 4,776,984, a concentrate enriched with fatty acids belonging to the n-6 family, more particularly GLA, is prepared from a mixture of fatty acids obtained by saponification of a seed oil containing GLA, for example blackcurrant seed oil. The process comprises saponifying the oil, fractionating the fatty acids by complexing with urea in the presence of methanol and extracting the fraction enriched with GLA using hydrochloric acid. It is possible by this process to obtain a GLA content of around 77 to 81% in the final fatty acid mixture.

If the above-mentioned mixture is to be further enriched, for example to obtain a polyunsaturated fatty acid content of at least 90% by weight, the fatty acids are normally subjected to chromatographic separation.

Application of the known process on an industrial scale has disadvantages: the methanol contaminates the end product by formation of toxic fatty acid methyl esters. In addition, the use of hydrochloric acid corrodes the installations.

SUMMARY OF THE INVENTION

The process according to the present invention is characterized in that the ethanolysis of an oil rich in polyunsaturated fatty acids refined beforehand is carried out with ethanol in the presence of a catalyst to obtain fatty acid ethyl esters, these esters are complexed with urea in solution in ethanol to form an insoluble inclusion complex, the inclusion complex is separated and a fatty acid ethyl ester fraction enriched with polyunsaturated fatty acids is collected in the liquid phase.

DETAILED DESCRIPTION OF THE INVENTION

In the context of the present invention, the expression "oil rich in polyunsaturated fatty acids" is understood to be a vegetable oil rich in GLA, for example evening primrose oil, borage oil or an oil of seeds of fruit of the genus Ribes, more particularly blackcurrant, a vegetable oil rich in linoleic acid (LA) and poor in alpha-linolenic acid (ALA), for example passion flower oil or corn oil or even a marine animal oil containing the acids EPA and DHA. When the oil is borage oil, for example, a final product concentrated in ethyl esters of polyunsaturated fatty acids may be obtained which contains ethyl esters of gamma-linolenic acid in an amount of at least 90% by weight of fatty acid esters in the product.

By "preliminary refining" is meant a series of treatments carried out conventionally after extraction of the oil, for example by pressing and solvent extraction of the press cake, for example with hexane, followed by evaporation of the hexane. These refining treatments comprise degumming, for example with silica gel, neutralization with a base, decoloration in vacuo in the presence of bleaching earth, deodorization by stripping with steam and stabilization by addition of a fat-solubilized antioxidant.

According to the invention, the refined oil is subjected to ethanolysis, i.e. the ethyl esters of the fatty acids are prepared by removing the glycerol from the acyl glycerols with ethanol in the presence of a suitable quantity of catalyst, for example sodium or potassium hydroxide or sodium ethylate. The ethanolysis is carried out by mixing the refined oil with 1.5 to 3 equivalents by weight, and preferably with around 2 equivalents by weight, of anhydrous ethanol in which 0.5 to 1% and preferably 0.8% of catalyst, based on the oil, has been dissolved. The reaction may be carried out with stirring for 10 to 60 minutes at a temperature of 30° to 80° C. and preferably at a temperature of around 50° C. After standing for about 1 hour, the presence of two liquid phases, namely a light phase containing the ethyl esters and a heavy phase containing the glycerol, is observed and the glycerol formed is separated by centrifugation or decantation.

This step is followed by fractionation of the ethyl esters by selective complexing of the mainly saturated and monounsaturated fatty acid ethyl esters with urea in the presence of ethanol, these esters forming insoluble inclusion complexes with the urea. Ethyl esters of fatty acids having a higher degree of unsaturation can also form insoluble complexes with the urea in dependence upon the cooling temperature, the quantity of urea, the position and the number of double bonds. The liquid phase is enriched with the desired polyunsaturated fatty acid esters. The quantity of urea used is proportional to the quantity of desired fatty acid ethyl esters in the liquid phase. A ratio by weight of ethyl esters to urea of 1:2 to 1:4.5 and preferably of the order of 1:3.2 is thus used. The quantity by weight of ethanol used is advantageously 6.5 to 15 times and preferably around 9.75 times the quantity of starting material employed.

To carry out this fractionation, the mixture of ethyl esters, urea and ethanol is heated with stirring to around 80° C. until the urea dissolves.

If it is desired to enrich the mixture with the ethyl esters of the polyunsaturated fatty acids GLA, EPA and DHA, for example, the solution is subsequently cooled to 0° to 20° C. and preferably to 15° to 18° C.

In the case of enrichment with LA for example, the solution is cooled to a higher temperature than before, for example to around 40° C.

A solid phase appears and is separated by centrifugation or filtration. The liquid phase is collected. The ethanol is partly eliminated from this liquid phase, after which the ethyl esters enriched with polyunsaturated fatty acids are extracted therefrom with a solvent, preferably n-hexane (hereinafter referred to as hexane). This extraction is preferably carried out in the presence of an acid, for example aqueous phosphoric acid. A crude concentrate of ethyl esters of polyunsaturated fatty acids is obtained in this way.

The solid phase still contains a significant quantity of the required ethyl esters which it is desirable to recover. To this end, these esters may be extracted from the solid complex with a solvent, for example hexane. The hexane may then be eliminated, for example by evaporation, and the ethyl esters thus recovered may be mixed with the batch intended for fractionation or may even be subjected to separate fractionation under the usual conditions to increase the yield. The residual esters present in the solid phase may be completely recovered by addition of water, a mineral acid and hexane. If this latter mixture is used as the starting material for fractionation, two successive fractionations are necessary, for example to obtain a concentrate containing more than 80% of GLA ethyl ester.

The crude concentrate thus prepared has to be refined. To this end, the concentrate is treated in solution, preferably in the form of a 20% solution in hexane, with 10 to 40% by weight and preferably with around 20% by weight of active carbon (based on the crude concentrate) at ambient temperature. After separation of the active carbon, for example by filtration, the hexane is eliminated, preferably by evaporation in vacuo, which leads to around 12% by weight of concentrate of polyunsaturated fatty acid ethyl esters, based on the oil used.

The concentrate thus refined may be stabilized against oxidation by addition of, for example, DL-alpha-tocopherol and ascorbyl palmitate dissolved in ethanol. After mixing, the ethanol and the remaining traces of hexane are removed from the concentrate by purging with nitrogen, for example at around 40° C. under an absolute pressure of approximately 300 mbar.

In one preferred embodiment of the process which leads to a final refined concentrate of fatty acid ethyl esters containing an extremely small or even negligible quantity of free fatty acids and, hence, a larger amount of polyunsaturated fatty acid esters, the ethanol is evaporated immediately after ethanolysis and, after separation of the glycerol, the ethanolyzate is pre-refined with active carbon in the presence of a solvent, preferably hexane, after which the solvent is eliminated, the other steps remaining unchanged.

The concentrate of ethyl esters of polyunsaturated fatty acids obtained by the process according to the invention may be used in the usual applications of polyunsaturated fatty acids, more particularly in nutritive, pharmaceutical, cosmetic and dermatological compositions, as described, for example, in European Patent No. 092 085 and in European Patent No. 092 076.

EXAMPLES

The invention is illustrated by the following Examples in which percentages are by weight, unless otherwise indicated.

Example 1

Seeds of borage (*Borago officinalis*) are extracted by mechanical pressing in the absence of heat, after which the oil is extracted from the press cake with hexane, followed by evaporation of the hexane. The crude oil is then refined by degumming with amorphous silica gel, neutralization with an aqueous sodium hydroxide solution, bleaching by contact with an activated bleaching earth in the presence of amorphous silica gel at 80° C. in a vacuum of 2 mbar, deodorization by stripping with steam in vacuo for 3 h at 180° C. and stabilization against oxidation by addition of ascorbyl palmitate. The borage oil has the approximate composition shown in Table 1 below:

TABLE 1

| Fatty acids | % of the fatty acids |
|---|---|
| C16:0 | 9–15 |
| C16:1 | <0.4 |
| C18:0 | 3–7 |
| C18:1, delta 9 | 15–19 |
| C18:2, delta 9,12 | 32–38 |
| C18:3, delta 6,9,12 (GLA) | 18–25 |
| C18:3, delta 9,12,15 (ALA) | <1 |
| C20:0 | <0.4 |
| C20:1, delta 9 | 2–4 |
| C22:1, delta 9 | 2–4 |

5.12 Kg of anhydrous ethanol (prepared by treatment under reflux for 30 minutes) containing 1.5% sodium hydroxide are added to 16 kg of refined borage oil in a stirrer-equipped reactor. The resulting mixture is stirred for 30 minutes at 50° C. After standing for 60 minutes, two liquid phases have separated. The glycerol formed at the bottom of the reactor, which is the heavy liquid phase, is eliminated by decantation and the light phase is collected.

A mixture consisting of 15.5 kg of the fatty acid ethyl esters representing the light phase, 154 kg of technical ethanol and 49.6 kg of urea is heated with stirring at 80° C. until a clear solution is formed. The mixture is then cooled to 15° C., a solid phase being formed. The solid phase is separated by filtration and 149.5 kg of clear liquid phase are collected. After elimination of 80 kg of ethanol by evaporation in vacuo, 80 kg of water, 40 g of an 80% aqueous phosphoric acid solution and 14 kg of hexane are added to the condensate. After stirring for 10 minutes, the mixture is left standing for 60 minutes, which produces two phases. The upper phase containing 15% of fatty acid ethyl esters is collected by decantation.

0.4 kg of active carbon is added to the solution of fatty acid ethyl esters in hexane. After stirring for 60 minutes at ambient temperature, the active carbon is separated by filtration and the hexane is eliminated by evaporation in vacuo. 1.8 kg of concentrate of fatty acid ethyl esters (corresponding to a yield of 12%, based on the starting oil) is thus obtained. The concentrate has the composition shown in Table 2 below, as determined by gas phase chromatography:

TABLE 2

| Fatty acid ethyl esters (EE) | % |
|---|---|
| C18:2, delta 9,12 | 2 |
| C18:3, delta 6,9,12 (GLA) | 95.9 |
| C18:3, delta 9,12,15 (ALA) | traces |
| C18:4, delta 6,9,12,15 | 0.8 |
| Others | 1.3 |

Finally, the refined concentrate is stabilized against oxidation by addition of 900 mg of DL-alpha-tocopherol and 360 mg of ascorbyl palmitate dissolved in ethanol to 1.8 kg of concentrate. After mixing, the ethanol and the remaining traces of hexane are eliminated from the concentrate by purging with nitrogen at 40° C. under an absolute pressure of 300 mbar.

Example 2

The esters of fatty acids of blackcurrant seed oil are fractionated in the same way as in Example 1. The composition of the concentrate obtained is shown in Table 3 below:

TABLE 3

| % GLA in the starting oil | % GLA—EE in the enriched fraction | Yield (%, based on GLA) |
|---|---|---|
| 15.7 | 74.4 | 56.5 |

Example 3

The procedure of Example 1 is applied to the fractionation of the ethyl esters of fatty acids from fish oil. Fish oil contains very long chain polyunsaturated fatty acids belonging to the n-3 family, mainly EPA and DHA.

The composition (%) of the fatty acid esters of the concentrate obtained is determined by gas phase chromatography and is shown in Table 4 below:

TABLE 4

| | Composition of the EE (%) | | | |
|---|---|---|---|---|
| | C18:4 | C20:5 | C22:6 | Others |
| Fish oil | 3.6 | 19.7 | 12.5 | 64.2 |
| Enriched fraction as ethyl ester | 8 | 49 | 27 | 16 |
| Yield (%, based on the initial quantity of fatty acid) | 47 | 52.6 | 45.7 | |

Example 4

Corn oil is selectively enriched with LA ethyl ester in the same way as in Example 1, except that the ratio of ethyl esters to urea is 1:2.7 as opposed to 1:3.2 and the fractionated mixture is cooled to 40° C. as opposed to 15° C. The initial LA content in the corn oil is 52.3% and the concentrate obtained contains 92.4% of LA-EE, corresponding to a yield of 59%, based on the initial quantity of LA.

Example 5

7.4 kg of anhydrous ethanol containing 1.95% sodium hydroxide in ethanol prepared beforehand by stirring the ethanol and the sodium hydroxide for 60 mins. at 50° to 60° C. are added to 18 kg of refined borage oil. The resulting mixture is then stirred for 60 minutes at 50° C., after which the excess ethanol is evaporated at 50° C. under an absolute pressure of 100 mbar. After leaving the mixture standing for 60 minutes, the heavy phase containing the glycerol, which has collected at the bottom of the reactor, is carefully separated.

The light phase obtained, which represents 17.5 kg of mixed ethyl esters, is dissolved in 35 kg of hexane and the resulting solution is added to a solution of 3.5 kg of active carbon over a period of 10 minutes with stirring at ambient temperature. After the spent active carbon has been eliminated by filtration and the hexane subsequently evaporated, 16.5 kg of pre-refined fatty acid ethyl esters are obtained.

A mixture of 161 kg of technical ethanol and 53 kg of urea is heated to 75° C. until the urea has completely dissolved. 16.5 kg of the pre-refined ethyl esters are then added to the ethanolic solution and the resulting mixture is cooled to 70° C. This results in the formation of a solid phase, which is separated by filtration, and 160 kg of a clear liquid phase which is collected. After elimination of 100 kg of ethanol by evaporation in vacuo, 60 kg of water, 0.18 kg of an 85% aqueous phosphoric acid solution and 12 kg of hexane are added to the mixture thus concentrated. After stirring for 10 minutes, the mixture is left standing for 60 minutes, after which 15.2 kg of light phase representing the ethanolyzate and containing 14.8% of fatty acid ethyl esters are collected by decantation.

At this stage, the ethanolyzate is pre-refined with 0.66 kg of active carbon. After stirring for 60 minutes at ambient temperature, the spent active carbon is eliminated by filtration and the hexane is eliminated by evaporation in vacuo. 2.19 kg of concentrate of GLA-EE are thus obtained.

1.06 g of DL-alpha-tocopherol and 0.42 g of ascorbyl palmitate dissolved in 6 g of ethanol are added to 2.19 kg of the concentrate. After adequate mixing, the ethanol and traces of residual hexane are eliminated by purging the concentrate with nitrogen for 4 h at 40° C. under an absolute pressure of 300 mbar.

The GLA-EE concentrate obtained contains more than 97% of fatty acid ethyl esters and less than 0.2% of free fatty acids. The concentrate has the composition shown in Table 5 below, as determined by gas phase chromatography:

TABLE 5

| Fatty acid ethyl esters (EE) | % |
|---|---|
| C18:2, delta 9,12 | 4.4 |
| C18:3, delta 6,9,12 (GLA) | 93.2 |
| C18:3, delta 9,12,15 (ALA) | traces |
| C18:4, delta 6,9,12,15 | 0.2 |
| Others | 2.2 |

We claim:

1. A process for obtaining a concentrate of polyunsaturated fatty acid ethyl esters from an oil comprising:
    mixing a refined oil rich in polyunsaturated fatty acids with anhydrous ethanol in the presence of a catalyst to obtain a reaction medium product comprising fatty acid ethyl esters;
    evaporating ethanol from the reaction medium and obtaining a fatty acid ethyl ester phase and a glycerol phase;
    separating the reaction medium fatty acid ethyl ester phase from the glycerol phase;
    combining the ethyl ester phase with hexane and with active carbon and refining the ethyl ester phase to obtain refined fatty acid ethyl esters and after refining, separating the active carbon from the refined esters and hexane and eliminating the hexane from the refined esters;
    mixing and heating the refined esters with urea and ethanol to form a urea complexing mixture and cooling the urea complexing mixture to obtain a liquid phase containing concentrated esters and a solid inclusion complex phase; and
    separating the liquid phase from the solid phase to obtain an isolated concentrate of polyunsaturated fatty acid ethyl esters.

2. A process for obtaining a concentrate of polyunsaturated fatty acid ethyl esters from an oil comprising:
    mixing a refined oil rich in polyunsaturated fatty acids with anhydrous ethanol in the presence of a catalyst to obtain a reaction medium product comprising a fatty acid ethyl ester phase and a glycerol phase;
    separating the fatty acid ethyl ester phase from the glycerol phase;
    mixing and heating the fatty acid ethyl ester phase with urea and ethanol to form a urea complexing mixture and cooling the urea complexing mixture to obtain a liquid phase containing fatty acid ethyl esters and a solid inclusion complex phase;
    separating the liquid phase from the solid phase;
    evaporating ethanol from the liquid phase to obtain a concentrate;
    combining the concentrate with hexane, water and a mineral acid and obtaining a hexane phase containing a further fatty acid ethyl ester concentrate; and
    adding active carbon to the hexane phase and refining the hexane phase to obtain a refined ester concentrate and after refining, separating the active carbon from the refined concentrate and hexane and eliminating the hexane from the refined esters to obtain an isolated concentrate of polyunsaturated fatty acid ethyl esters.

3. A process according to claim 1 or 2 wherein the refined oil and ethanol are mixed at a temperature of from 30° C. to 80° C. and wherein the urea complexing mixture is cooled to a temperature of from 0° C. to 20° C.

4. A process according to claim 1 or 2 wherein the refined oil and ethanol are mixed at a temperature of from 30° C. to 80° C. and wherein the urea complexing mixture is cooled to a temperature of from 15° C. to 18° C.

5. A process according to claim 1 or 2 wherein the refined oil and ethanol are mixed at a temperature of from 30° C. to 80° C. and wherein the urea complexing mixture is cooled to a temperature of about 40° C.

6. A process according to claim 1 or 2 further comprising extracting fatty acid ethyl esters from the solid phase.

7. A process according to claim 1 or 2 further comprising adding a fat-soluble antioxidant to the concentrate.

8. A process according to claim 1 or 2 wherein the refined oil is selected from the group consisting of refined evening primrose oil, borage oil and blackcurrant seed oil.

9. A process according to claim 1 or 2 wherein the refined oil is selected from the group consisting of refined passion flower oil and corn oil.

10. A process according to claim 1 or 2 wherein the refined oil is a refined marine animal oil containing eicosapentaenoic acid and docosahexaenoic acid.

* * * * *